United States Patent [19]

Weissman

[11] Patent Number: 5,017,137

[45] Date of Patent: May 21, 1991

[54] DENTAL TOOL REAMER CAPABLE OF FOLLOWING NATURAL CURVATURE OF TOOTH CANAL

[76] Inventor: Bernard Weissman, 225 E. 48th St., New York, N.Y. 10017

[21] Appl. No.: 580,896

[22] Filed: Sep. 11, 1990

Related U.S. Application Data

[63] Continuation of Ser. No. 273,377, Nov. 18, 1988, abandoned.

[51] Int. Cl.⁵ .................................................. A61C 5/02
[52] U.S. Cl. ..................................... 433/102; 433/224; 433/165
[58] Field of Search ................ 433/224, 102, 165, 166

[56] References Cited

U.S. PATENT DOCUMENTS

| | | | |
|---|---|---|---|
| 453,254 | 6/1891 | Bryant | 433/165 |
| 503,744 | 8/1893 | How | 433/165 |
| 1,307,446 | 6/1919 | Kerr | 433/102 |
| 1,499,970 | 7/1924 | Bush | 433/165 |
| 2,715,772 | 8/1955 | Fritz | 433/165 |
| 2,902,763 | 9/1959 | Heppe | 433/165 |
| 4,661,061 | 4/1987 | Martin | 433/102 |
| 4,684,346 | 8/1987 | Martin | 433/102 |

FOREIGN PATENT DOCUMENTS 2649209  5/1978  Fed. Rep. of Germany ...... 433/165

*Primary Examiner*—Gene Mancene
*Assistant Examiner*—Adriene B. Lepiane
*Attorney, Agent, or Firm*—Paul J. Sutton; Barry G. Magidoff; Anthony Amaral, Jr.

[57] ABSTRACT

The present invention provides a dental tool which operates as a reamer, while reducing the danger of removing excessive tooth material when boring out the tooth canal. The dental tool includes a first holder end portion designed to be receiveable in a dental tool holder, such that the dental tool holder can rotate the dental tool; a second reaming end portion having a polygonal cross-section and cutting edges tapering longitudinally endwardly to a minimum effective cutting diameter plane, or a point, from a plane of maximum effective cutting diameter, and optimally also having reverse cutting surfaces tapering longitudinally in the opposite direction to an inner plane of reduced effective cutting diameter; and a shank portion extending between the two end portions. The plurality of reamer cutting edges extend axially, and are designed for reaming out a bore into a tooth canal of a patient upon rotation of the tool. The shank portion has an effective cross-section diameter along its length which is smaller than the diameter at the plane of maximum effective cutting diameter or at the plane of reduced effective cutting diameter of the reaming end portion. Most preferably, the shank tapers inwardly towards the first holder end portion, such that the plane of smallest diameter of the shank is located adjacent the first holder end portion.

8 Claims, 2 Drawing Sheets

DENTAL TOOL REAMER CAPABLE OF FOLLOWING NATURAL CURVATURE OF TOOTH CANAL

This is a continuation of application Ser. No. 273,377 filed Nov. 18, 1988 and abandoned Sept. 13, 1990.

BACKGROUND OF THE INVENTION

The present invention relates to a tool for use in dentistry, and more particularly to a dental tool which provides for the forming of a bore hole by generally following the natural canal of a tooth. The tool can be rotated by a dental handpiece commonly used in dentistry.

It is well known procedure in the dental art to form a bore hole by widening the natural opening in the root canal of a tooth using a reaming tool; it is also common to reduce the upper surface of the tooth, using a dental grinding tool to provide a surface for supporting a dental crown or prosthesis to be secured integral to the tooth via a cemented anchor post, extending into and cemented within the bored out root canal. A problem can arise as a result of the natural curvature, in an axial direction, of the tooth canal. It is difficult for such conventional such tools to avoid cutting away too much tooth material at the point of greatest curvature of the canal.

SUMMARY OF THE INVENTION

Accordingly, it is an object of the present invention to provide a dental tool which operates as a reamer, while reducing the danger of removing excessive tooth material when boring out the tooth canal It is a further object of the present invention to provide a dental tool which naturally follows the contour of the tooth root canal.

These and other objects are achieved in accordance with the present invention wherein the dental tool includes a first holder end portion designed to be receivable in a dental tool holder, such that the dental tool holder can rotate the dental tool; a second reaming end portion having cutting edges tapering longitudinally endwardly to a minimum effective cutting diameter plane, or a point, from a plane of maximum effective cutting diameter, and optimally also having reverse cutting surfaces tapering longitudinally in the opposite direction to an inner plane of reduced effective cutting diameter, the plurality of reamer cutting edges, extending axially, for reaming out a bore into a tooth canal of a patient upon rotation of the tool; and a shank portion extending between the two end portions, the shank portion having a cross-section diameter along its length which is smaller than the diameter at the plane of maximum effective cutting diameter or at the plane of reduced effective cutting diameter of the boring end portion. Most preferably, the shank tapers inwardly towards the first holder end portion, such that the plane of smallest diameter of the shank is located adjacent the first holder end portion.

The dental tool of the present invention is to be used with a conventional dental tool handpiece as providing support and driving power for the dental tool. As used, the drill point, or reamer, is placed within the root canal opening of a reduced tooth. The tooth has previously been ground down to approximately the desired height above the gum line by removing broken or decayed dental material. The tool is held by a conventional dental handpiece and the power applied to rotate the tool in a conventional manner, pressing downwardly against the tooth to bore out a hole of the desired depth. The narrower shank permits slanting of the tool as it moves into the root canal to form the bore hole, enabling the cutting tip to generally follow the natural curvature of the tooth canal as it is pressed inwardly.

It is well known in the dental art to select a reamer of a proper length and diameter to obtain the desired size bore hole. In the present invention, however, the length of the tool is not limited to the depth of the bore hole desired. A separate tool can be used for counterboring and grinding, to form a desired funnel-shaped enlargement of the entrance to the bore hole, and a platform grinding tool which makes contact with the top surface of the tooth to form the desired flat platform surrounding the bore, and most preferably extending a certain distance below the surface of the surrounding tooth material.

After forming the enlarged counterbore at the top of the bore hole and grinding down the tooth surface to form a flat platform around the outer opening to the bore in the tooth, perpendicular to the central axis of the bore, an anchor post for a dental prosthesis can then be inserted into the bore hole.

Further details of the present invention are shown in the accompanying drawings, by way of example and not by way of exclusion. Some portions of the invention, or the context therefor, are shown in schematic representation, where greater detail is unnecessary as it will be apparent or well-known to those skilled in the art. Referring to the accompanying drawings:

DETAILED DESCRIPTION OF THE INVENTION

Figure 1:
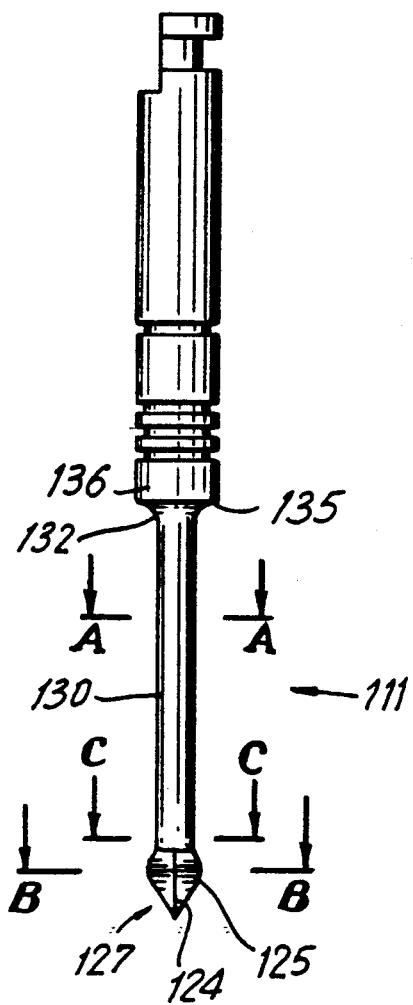
FIG. 1 is a side elevation view of one embodiment of the present invention.
Figure 5:
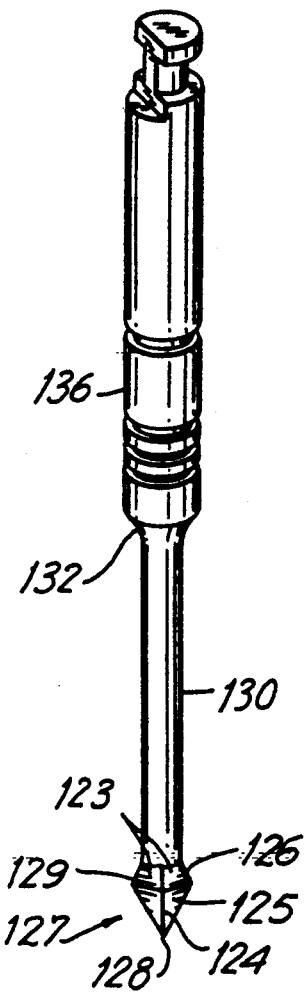
FIG. 5 is a perspective view showing a tool of the present invention.
Figure 2:
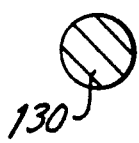
FIG. 2 is a cross-section view taken along line A—A of FIG. 1.

Referring to the drawings, a combination tool, generally indicated by the numeral 111, is shown having a reaming, or cutting, tip, generally indicated by the numeral 127, at one end, a holder 136, at the other end, and a shank 130 therebetween. The holder portion 136 is of conventional design suitable for being secured to conventional dental handpieces, and can be modified or adapted for whichever dental handpiece is to be used.

The cross-sections of the cutting sections, i.e., the cutting tip 127 and the return cutting section 126, are substantially polygonal, most preferably square (as shown) or triangular, but preferably not having more than six sides, and the preferred cross-section of the shank 130 is round.

Figure 3:
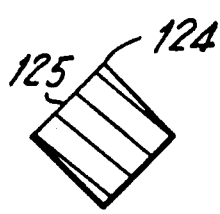
FIG. 3 is a cross-elevation view taken along line B—B of FIG. 1.
Figure 4:
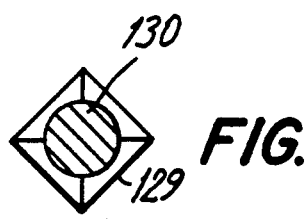
FIG. 4 is a cross-section view taken along lines C—C of FIG. 1.

When the term "diameter" is used for such polygonal cross-sections, it refers to the "effective diameter", i.e., the diameter of a bore hole cut by such sections rotating about a single axis. The cross-section views of FIGS. 3 and 4 shows that both portions of the routing or cutting tip 127 are substantially square in cross-section.

The cutting tip 127 is faceted and has two sets of four facets 123, 125. The outer facets 125, each substantially triangular, extend from the plane of maximum diameter 129 to the tip end 128; the inner facets 123, each truncated triangles, extend from the plane of maximum diameter 129 to the beginning of the shank 130. Each facet in the two sets 123, 125 intersects the adjoining facet along a sharp cutting edge 124, 126, the interface 129 between the two sets of facets 123, 125 preferably is a continuous curve.

The cutting tip 127 can be optionally coated at its apices 124, 126, or all along the facets 125, 123 as well, with a hard, fine granular material, such as diamond dust, if desired, to increase durability and reaming effectiveness.

Figure 6:
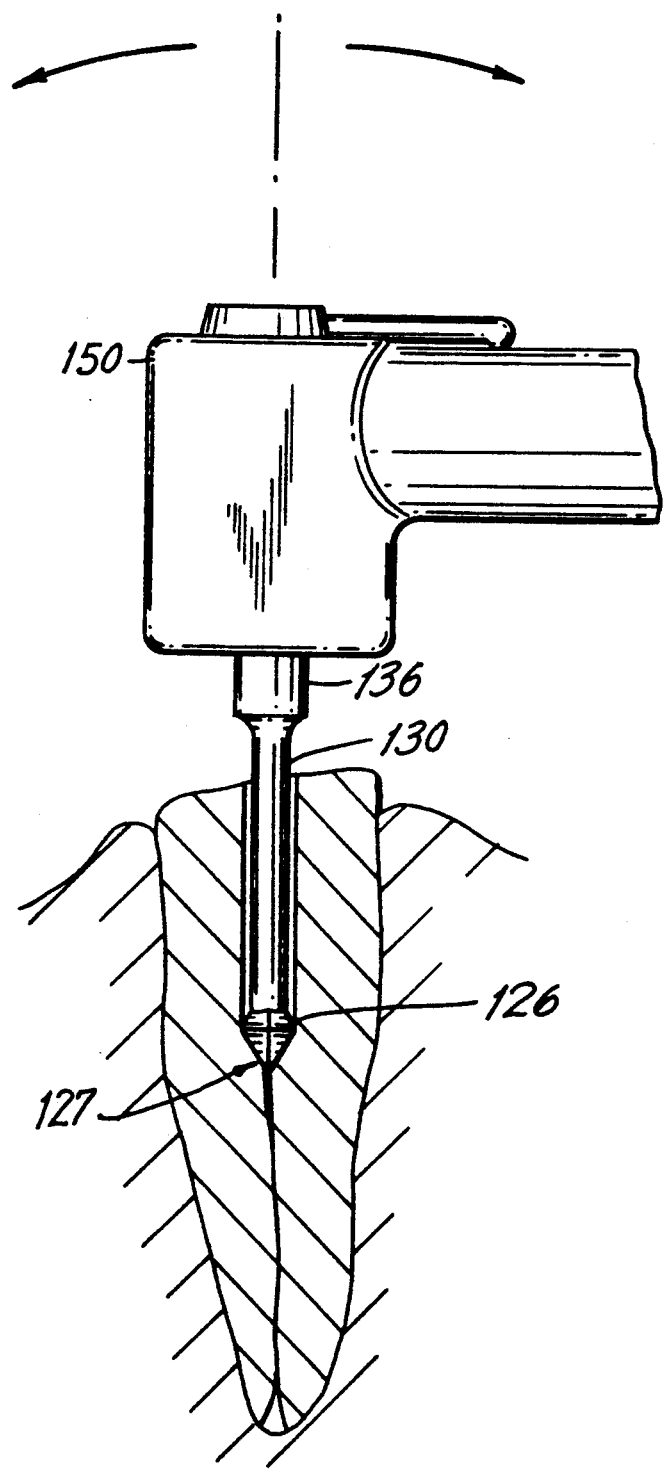
FIG. 6 is a partial cross-section elevation view showing a tool of the present invention deployed within the partially bored canal of a tooth stub.

Referring to FIG. 6, wherein the tool of the present invention is located within a partially bored tooth canal, the tool is operatively supported and held by a conventional handpiece, generally indicated by the numeral 150. The handpiece is of a conventional type, which provides support and carries the driving power to the tool to cause it to rotate. The handpiece 150 can securely hold and mechanically drive the tool, while being subjected to longitudinal force axially into the tooth, during a reaming out operation. Such hand tools are well-known, and can, e.g., be air or motor driven, or directly gear driven, by straight or right angle dental rotary devices.

The maximum effective diameter of the cutting tip 127 is at least about 15%, and most preferably at least about 25%, larger than the diameter of the shank 130. Most preferably, the shank 130 is tapered inwardly from the cutting tip to the counterbore portion 132, such that the minimum diameter of the shank is preferably just adjacent the section 136. In this manner the structurally weakest point of the tool is at the upper end of the shank 130. The degree of taper need only be about at least 0.5 degree and preferably about 1 degree.

As is shown by FIG. 6, the relatively narrow shank 130 permits the cutting tip to change directions in the middle of a bore hole so as to follow the natural curvature of a tooth canal. As such curvature is relatively small, an approximately 20–25% difference in diameter is usually sufficient to permit following such curvature.

The return cutting section 126, adjacent the shank 130, provides for cutting in the reverse direction, when withdrawing the tool. This prevents locking in of the tool in a tooth bore, and eases removal after reaming.

In carrying out the procedure in accordance with the present invention, after the bore is fully formed in the tooth, a counterbore and a flat platform surface can also be formed surrounding the bore and below the top surface of the tooth.

Referring, by way of example to the dental tool of the drawings, the maximum effective diameter of the cutting tip 127 is generally in the range of from about 0.03 inch to about 0.08 inch, e.g., about 0.06 inch; the diameter of the shank is preferably about 60% to about 80% of the maximum diameter of the cutting tip 127, e.g., from about 0.025 inch to about 0.052 inch. The maximum effective diameter of a counterbore is usually about 50% greater than that of the cutting tip 127, e.g., about 0.09 inch, and the outer diameter of the annular planar grinding surface around the counterbore is about 30% to about 50% larger again, e.g., about 0.12 inch.

The tool can be formed of stainless steel, or other hard material, and coated with a fine granular abrasive, e.g., diamond dust, if desired.

The Patentable Embodiments of the Invention which are claimed are as follows:

1. A dental tool for the boring out of a tooth canal following its natural curvature, the tool comprising a first holder end portion and a second cutting end portion; and an intermediate shank portion interconnecting the two end portions; the holder end portion being designed to be receivable in a dental tool holder such that the dental tool holder can rotate the dental tool; the second cutting end portion having a continuously varying effective cross sectional diameter transverse to the longitudinal axis, the effective cross sectional diameter increasing from a tip having a minimum effective diameter to a plane of maximum effective cutting diameter and reducing thereafter to a plane of reduced effective cutting diameter in the direction from the second cutting end portion to the first holder end; the surface of the cutting end between the tip of minimum effective diameter and the plane of maximum effective cutting diameter being substantially triangular facets intersecting along sharp cutting edges extending from the plane of maximum effective cutting diameter to the tip, and the surface of the cutting end between the plane of maximum cutting diameter and the reduced effective cutting diameter being truncated triangles, intersecting along sharp cutting edges extending up to the shank portion; the shank portion having a diameter less than that of the maximum effective cutting diameter, and not greater than the reduced effective cutting diameter; such that the tool generally follows the natural curvature of the tooth canal when rotated within the canal, by permitting swiveling of the tool shank laterally within the tooth canal while reaming out the canal so as to increase the internal diameter of the tooth canal.

2. The dental tool of claim 1 wherein the shape of a lateral cross-section of the shank is substantially circular.

3. The dental tool of claim 1 wherein the shape of a lateral cross-section of the cutting end portion, intermediate the tip and the plane of reduced effective cutting diameter, is a regular polygon.

4. A dental tool of claim 3 wherein the polygonal cross-section of the cutting end portion has from three to six sides.

5. The tool of claim 1 wherein the surfaces adjacent the plane of maximum effective diameter define a substantially continuous curve.

6. The tool of claim 1 wherein the triangular facets are grinding surfaces coated with relatively hard and fine granular material.

7. The dental tool of claim 1 wherein the maximum effective diameter of the cutting end portion is at least about 25% larger than the diameter of the shank.

8. The dental tool of claim 7 wherein the shank tapers from the plane of reduced effective cutting diameter towards the holder end portion to a minimum shank diameter adjacent the holder end portion.

* * * * *